United States Patent
Cawse

(10) Patent No.: US 9,296,857 B2
(45) Date of Patent: Mar. 29, 2016

(54) CURING AGENTS

(75) Inventor: John Cawse, West Wratting (GB)

(73) Assignee: Hexcel Composites Limited, Duxford (GB)

( * ) Notice: Subject to any disclaimer, the term of this patent is extended or adjusted under 35 U.S.C. 154(b) by 766 days.

(21) Appl. No.: 13/636,317

(22) PCT Filed: Mar. 21, 2011

(86) PCT No.: PCT/GB2011/050554
§ 371 (c)(1),
(2), (4) Date: Sep. 20, 2012

(87) PCT Pub. No.: WO2012/033766
PCT Pub. Date: Mar. 15, 2012

(65) Prior Publication Data
US 2013/0102756 A1    Apr. 25, 2013

(30) Foreign Application Priority Data
Mar. 24, 2010 (GB) ................................ 1004940.1

(51) Int. Cl.
- C08G 59/14 (2006.01)
- C08G 59/50 (2006.01)
- C07C 211/60 (2006.01)
- C07D 209/08 (2006.01)
- C07D 215/06 (2006.01)

(52) U.S. Cl.
CPC .......... *C08G 59/1477* (2013.01); *C07C 211/60* (2013.01); *C07D 209/08* (2013.01); *C07D 215/06* (2013.01); *C08G 59/5033* (2013.01)

(58) Field of Classification Search
CPC ........... C08G 59/5073; C08G 73/1085; C08K 5/3442; C07D 215/06; C07C 211/60
USPC ....................................... 528/403
See application file for complete search history.

(56) References Cited

U.S. PATENT DOCUMENTS

| 4,427,802 A | 1/1984 | Moulton et al. |
| 4,629,777 A | 12/1986 | Pfeifer |
| 4,680,195 A | 7/1987 | Pfeifer |
| 5,246,606 A | 9/1993 | Evans |

FOREIGN PATENT DOCUMENTS

| EP | 0171588 A1 | 2/1986 |
| EP | 1454936 A1 | 9/2004 |
| EP | 1698612 A1 | 9/2006 |
| GB | 806817 | 12/1958 |
| JP | 03081278 A | 4/1991 |

OTHER PUBLICATIONS

Gerzeski, R: "Attempts to Enhance the Properties of EPON 830-4, 4'-methylene Bis Cyclohexylamine Epoxy Resin Systems by Exposing Them to 0.1290 to 0.8810 Tesla Magnetic Fields While Thermally Curing Them", Polymer Engineering and Science, Brookfield Center, US, vol. 39, pp. 2150-2158, Nov. 1, 1999.
Acta Crystallographica, Section E: Structure Reports Online, vol. E64(9), 2008. p. 1747.
Khimiko-Farmatsevticheskii Zhurnal, 1984, vol. 18, No. 1,pp. 29-3-ISSN: 0023-1134.
Chemical & Pharmaceutical Bulletin, vol. 12, No. 6, 1965, pp. 677-682.

*Primary Examiner* — Megan McCulley
(74) *Attorney, Agent, or Firm* — W. Mark Bielawski; David J. Oldenkamp

(57) ABSTRACT

A curable resin comprising a compound having the structure

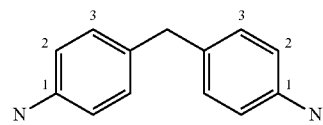

wherein each carbon 2, together with either its carbon 1 or carbon 3, are members of a fused cycloaliphatic ring, and when carbon 1 is a member of the ring so is N, and wherein each of the aliphatic or aromatic ring-member carbons may either be members of further fused cycloaliphatic rings or be bonded to a group selected from H or linear or branched $C_1$ to $C_5$ alkyl.

19 Claims, No Drawings

CURING AGENTS

TECHNICAL FIELD

The present invention relates to novel resin curing agents, particularly for epoxy and urethane resins.

BACKGROUND

Curable resin systems are widely known and have a wide range of uses in a variety of technical fields. These systems function by reaction between resin molecules and curing agents. Upon activation, e.g. by mixing together or by heating, functional groups on the curing agent react with functional groups on the resin molecule to form an extended polymeric network, which is the process known as curing.

The resulting cured resin has physical properties which are largely or entirely dictated by the choice of resin, the choice of curing agent and the curing regime employed. A wide variety of physical properties can be obtained by altering one or more of these variables.

A particularly useful physical property is for the cured resin to be mechanically tough and able to withstand an impact without brittle fracture. Such resins are particularly useful when involved in the manufacture of a structure.

However, it is known that cured resins which are tough generally tend to have a low glass transition temperature, which can make them unsuitable for use in structures. Known methods of increasing the glass transition temperature, generally involve the material becoming more brittle, which is again not appropriate for use in structures. Additionally, known methods of toughening a brittle resin usually also reduce the glass transition temperature.

It would therefore appear that cured resin systems which are both mechanically tough and yet have a high glass transition temperature, so that they can be used in structural applications, are not readily achievable with known systems.

SUMMARY OF THE INVENTION

In a first aspect, the present invention relates to curable resin comprising a compound having the structure

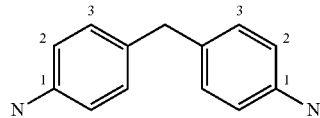 [SMILES: Nc1ccc(Cc2ccc(N)cc2)cc1]

(I)

wherein each carbon 2, together with either its carbon 1 or carbon 3, are members of a fused cycloaliphatic ring, and when a carbon 1 is a member of the ring so is N, and wherein each of the aliphatic or aromatic ring-member carbons may either be members of further fused cycloaliphatic rings or be bonded to a group selected from H or linear or branched $C_1$ to $C_5$ alkyl.

Compounds according to the invention have been found to be excellent curing agents, particularly for epoxy and urethane systems. It is believed that the presence of the cycloaliphatic groups provides a rigidity to the curing agent which translates into a higher glass transition temperature in the cured resin system.

Surprisingly, this increase in glass transition temperature is not accompanied by an increase in the brittleness of the cured resin systems.

Any carbons forming part of any further fused cycloaliphatic rings may also be bonded to either an H or linear or branched $C_1$ to $C_5$ alkyl. Preferably each of the aliphatic or aromatic ring-member carbons in the compound are bonded to an H or a linear or branched $C_1$ to $C_4$ alkyl. More preferably they are bonded to an H or linear or branched $C_1$ to $C_3$ alkyl, most preferably they are bonded to an H, $C_1$ or $C_2$ alkyl.

Thus, the compounds preferably have a molecular weight of no greater than 600, more preferably no greater than 500, most preferably no greater than 400, and optimally no greater than 350.

The cycloaliphatic rings typically comprise five or six carbons, preferably six. Typically, each cycloaliphatic ring consists of only carbon atoms.

The compound is an amine, typically a diamine, with each N being bonded to an appropriate number of hydrogens.

In a first preferred embodiment, the compounds are primary aromatic amines of the type:

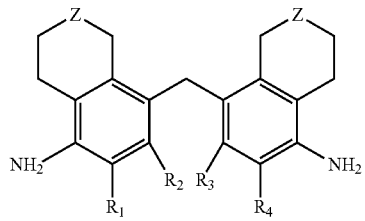

In a second preferred embodiment, the compounds are secondary aromatic amines of the type:

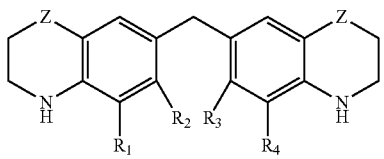

In these embodiments, Z may be a carbon atom or a single bond (i.e. the cycloaliphatic rings may be five or six membered).

Optionally, $R_1$ and $R_2$ (and likewise $R_3$ and $R_4$) can form part of a further cycloaliphatic ring.

In another embodiment, carbon 2 may be a member of two fused cycloaliphatic rings, one with carbon 1 and the other with carbon 3. Other arrangements may also be possible.

The curing agents may be conveniently employed whenever an amine-functional curing agent is required. They are therefore particularly suitable as curing agents in epoxy and urethane systems.

Suitable epoxy resins may comprise monofunctional, difunctional, trifunctional and/or tetrafunctional epoxy resins.

Suitable difunctional epoxy resins, by way of example, include those based on; diglycidyl ether of bisphenol F, diglycidyl ether of bisphenol A (optionally brominated), phenol and cresol epoxy novolacs, glycidyl ethers of phenol-aldehyde adducts and other aromatic epoxy resins, glycidyl ethers of aliphatic diols, diethylene glycol diglycidyl ether, aromatic epoxy resins, aliphatic polyglycidyl ethers, epoxidised olefins, brominated resins, aromatic glycidyl amines, heterocyclic glycidyl imidines and amides, fluorinated epoxy resins, glycidyl esters or any combination thereof.

Difunctional epoxy resins may be preferably selected from diglycidyl ether of bisphenol F, diglycidyl ether of bisphenol A, diglycidyl dihydroxy naphthalene, diglycidyl esters or any combination thereof.

Suitable trifunctional epoxy resins, by way of example, may include those based upon phenol and cresol epoxy novolacs, glycidyl ethers of phenol-aldehyde adducts, aromatic epoxy resins, aliphatic triglycidyl ethers, dialiphatic triglycidyl ethers, aliphatic polyglycidyl ethers, epoxidised olefins, brominated resins, triglycidyl aminophenyls, aromatic glycidyl amines, heterocyclic glycidyl imidines and amides, fluorinated epoxy resins, or any combination thereof.

Suitable tetrafunctional epoxy resins include N,N,N',N'-tetraglycidyl-m-xylenediamine (available commercially from Mitsubishi Gas Chemical Company under the name Tetrad-X, and as Erisys GA-240 from CVC Chemicals), and N,N,N',N'-tetraglycidylmethylenedianiline (e.g. MY721 from Huntsman Advanced Materials), and alkyl substituted and halogen substituted derivatives thereof.

As well as their use for forming polymers with epoxy compounds, the molecules of the present invention can be used for the formation of urethane type polymers or urethane-urea polymers. Suitable isocyanates for forming said polymers include diphenylmethane diisocyanate (MDI) in either a pure crystalline form or in a crude, polymeric form; toluene diisocyanate (TDI); isophorone diisocyanate (IPDI); xylyenediisocyanate; hexanediisocyanate and others well known in the art. Dimerised and trimerised isocyanates may also be present. There may also be present polyols for the development of soft segments, for example, high molecular weight polyether polyols, including hydroxyl functional polytetramethylene oxide, polypropylene oxide and polyethylene oxide or polyester polyols including polycaprolactone diols; and low molecular weight hydroxyl compounds such as glycerol, trimethylol propane, ethyleneglycol, butanediol and the like for the development of crosslinks or hard segments. Other amines, both primary and secondary, may optionally be present. Solid elastomers, thermoplastics, adhesives or foams may be formed depending on the conditions employed and the presence of appropriate additives for example, catalysts, water or other blowing agents, fillers or others commonly used in urethane technology.

The curing agents are particularly useful for structural applications. In such applications it is advantageous for the materials to have a moderately high melting point, particularly if the formulation is to be stored prior to cure for any length of time at ambient temperature. Thus, in a preferred embodiment, the curing agents have a melting point of from 80° C. to 200° C.

For some structural applications, liquid curable resin formulations are preferred, for example a fabrication method known as Resin Transfer Moulding (RTM) may be used. In such cases it may be preferable for the curing agents to be liquid at room temperature or to have melting points below 100° C.

The secondary aromatic amines are of particular interest. As they have only two reactive amine hydrogens, they are di-functional. This results in a lower cross-link density in the resulting cured resin, providing greater toughness. However, surprisingly this is accompanied by relatively high glass transition temperatures, suitable for use in highly demanding structural applications, such as aerospace.

As the materials are useful in structural applications, they are particularly suitable as a component of a prepreg. A prepreg comprises a fibre structure pre-impregnated with curable resin and curing agent, among other materials. Typically a number of plies of such prepregs are "laid-up" as desired and the resulting laminate is cured to produce a cured composite laminate.

Thus, the invention also relates to a prepreg comprising structural fibres, curable resin and a curing agent as described herein.

The fibres in the structural fibre layers of the perform may be uni-directional, fabric form or multi-axial. The arrangement of the fibres in neighbouring layers may be orthogonal to each other in a so-called 0/90 arrangement, signifying the angles between neighbouring fibre layers. Other arrangements such as 0/+45/−45/90 are of course possible among many other arrangements.

The fibres may comprise cracked (i.e. stretch-broken), selectively discontinuous or continuous fibres.

The structural fibres may be made from a wide variety of materials such as glass, carbon, graphite, metallised polymers aramid and mixtures thereof. Carbon fibres are preferred.

Curing may be carried out in any suitable method known in the art, and as the curable resins are typically thermosetting resins, this is preferably achieved by exposure to elevated temperatures and optionally elevated pressure.

The resulting cured resin preferably has a glass transition temperature of greater than 100° C., preferably greater than 120° C., more preferably greater than 140° C.

The invention will now be illustrated, by way of example.

EXAMPLES

Several compounds are preferred, specifically:

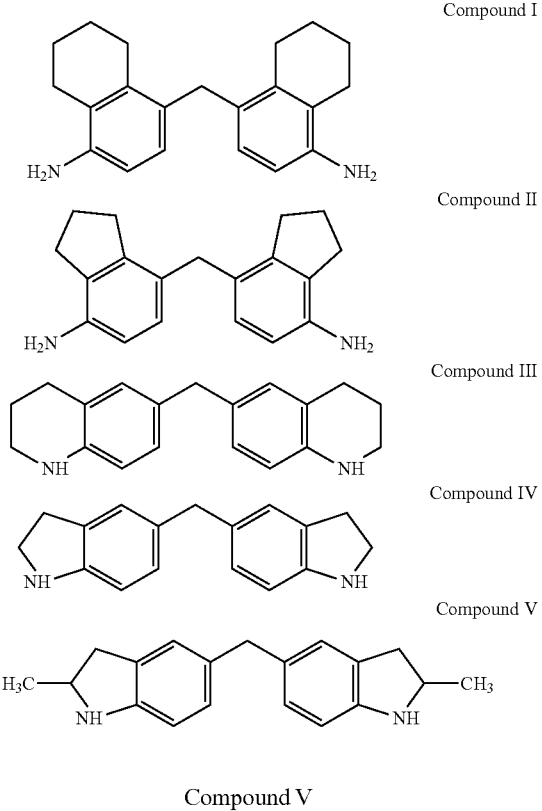

Compound V

The compounds have all been prepared via the acid catalysed condensation of the parent aniline derivative with formaldehyde solution. Preparative details of these compounds now follow.

Compound I

To 25 grams of 5,6,7,8-tetrahydro-1-naphthylamine in 74 ml of an acid medium consisting of 29 ml propan-2-ol, 36 ml water and 9 ml concentrated sulfuric acid and maintained at 60° C. was added 7.5 ml formalin solution (35%) over a period of 1 hour. The mixture was heated a further 3.5 hours then cooled, neutralized and the product triturated with water. The resulting soft solid was converted to the sulfate salt, washed with acetone, filtered, the free amine regenerated with ammonia solution and the resulting pinkish powder washed with water and dried to yield a beige solid, melting between 80 and 120° C.

Compound III

In a 5 liter flask maintained at 60° C., 500 grams of 1,2,3,4-tetrahydroquinoline was added to a mixture of 188 ml concentrated sulfuric acid, 428 ml of propan-2-ol and 793 ml of water. With mechanical stirring 162.4 g of 35% formalin solution was added dropwise over 70 minutes. The reaction was continued for 3 hours then cooled and neutralised with ammonia solution, forming a yellow granular solid. The solid was filtered off and boiled out with industrial methylated spirit (IMS) then the slurry was cooled and filtered. After drying there was obtained 416 grams (80% of theory) of a yellow solid, melting between 120-122° C.

NMR: DMSO d6, 400 MHz, 1.75 ppm (m, 4H, CH2), 2.6 (t, 4H, CH2), 3.15 (m, 4H, CH2), 3.5 (s, 2H in CH2 bridge) 5.37 (s, 2H, NH), 6.32 (d, 2H, aromatic 5-CH), 6.65 (m, 4H, aromatic CH)

FTIR: 3389, 2925, 2613, 1613, 1512, 1316, 807 $cm^{-1}$

MS: 278 (molecular ion, 100%); 249 (15%); 146 (loss of tetrahydroquinoline, 72%)

Compound IV

In a 1 liter flask 100 grams of indoline was added to 315 ml of an acid stock solution made from 194 ml propan-2-ol, 359 ml water and 85 ml concentrated sulphuric acid. To the slightly cloudy solution, at 60° C. was added over 1 hour, 36.3 grams of 35% formalin. The mixture was reacted for a further 4 hours, cooled and extracted with ethyl acetate. On evaporation a beige powder was obtained which was filtered and washed with water and a brown liquid phase removed. The product was dissolved in a small volume of IMS yielding white crystals. After filtering and drying, a total of 54 g white crystals were obtained from the first fraction and from the mother liquor. Melting point 92-93° C.

FTIR: 3344, 2892, 2843, 1610, 1492, 1248, 816, 768, 735, 693 $cm^{-1}$

MS: 250 (molecular ion, 100%); 132 (loss of indoline, 43%); 119 (loss of CH3, 23%)

Compound V

The above method was repeated using 100 g 2-methylindoline in place of the indoline, 282 ml of acid stock solution and 32.48 g of formalin. A brown oil was isolated which did not crystallise.

FTIR: 3360, 2959, 2924, 2840, 1616, 1492, 1250, 1103, 805.1 $cm^{-1}$

MS: 278 (molecular ion, 66%); 146 (loss of methyl indoline, 100%); 130 (loss of methyl, 18%)

Preparation of Thermosetting Polymers from Epoxy Resin

Each of the compounds prepared above was reacted with epoxy resin MY721 (available from Huntsman, UK) at stoichiometric equivalence using a standard cure cycle of 2 hours at 180° C. The Tgs of the resulting polymers were measured by DMA and were as follows (measured from the onset on the storage modulus curve):

TABLE 1

| Compound | E' Tg, ° C. |
|---|---|
| I | 211 |
| III | 173 |
| IV | 161 |
| V | 152 |

The above figures show that favourable Tgs can be obtained with these novel compounds.

What is claimed is:

1. A curable resin comprising a compound having the structure:

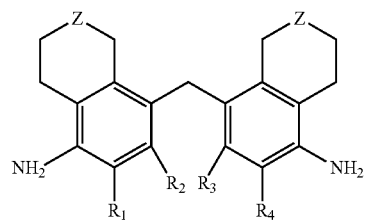

wherein Z is a carbon atom or a single bond and wherein $R_1$, $R_2$, $R_3$ and $R_4$ are H or a linear or branched $C_1$ to $C_5$ alkyl or wherein $R_1$ and $R_2$ form part of a further fused cycloaliphatic ring or wherein $R_3$ and $R_4$ form part of a further fused cycloaliphatic ring.

2. A curable resin according to claim 1, wherein any carbons forming part of any further fused cycloaliphatic rings are also bonded to either an H or linear or branched $C_1$ to $C_5$ alkyl.

3. A curable resin according to claim 1, wherein the compound has a molecular weight of no greater than 600.

4. A curable resin according to claim 1, having a melting point of from 80° C. to 200° C.

5. A curable resin according to claim 1, wherein the curable resin is an epoxy or urethane.

6. A curable resin according to claim 1, comprising a fibre reinforcement.

7. A curable resin according to claim 6, which is a prepreg.

8. A cured resin made by exposing a curable resin according to claim 1 to elevated temperature.

9. A cured resin according to claim 8, which has a glass transition temperature of greater than 100° C.

10. A cured resin according to claim 8 which forms part of a structural member of an aerospace structure.

11. A curable resin according to claim 1 wherein said compound has the structure:

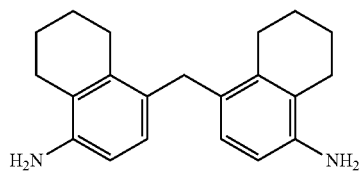 [SMILES: Nc1ccc(Cc2ccc(N)c3c2CCCC3)c2c1CCCC2]

such that Z is a carbon atom and $R_1$, $R_2$, $R_3$ and $R_4$ are H.

12. A curable resin according to claim 1 wherein said compound has the structure:

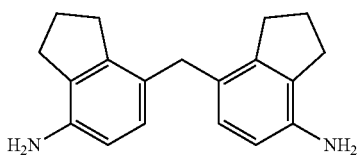 [SMILES: Nc1ccc(Cc2ccc(N)c3c2CCC3)c2c1CCC2]

such that Z is a single bond and $R_1$, $R_2$, $R_3$ and $R_4$ are H.

13. A curable resin according to claim 1 wherein $R_1$ and $R_2$ form part of a further fused cycloaliphatic ring.

14. A curable resin according to claim 13 wherein the fused cycloaliphatic rings comprise five or six carbons.

15. A curable resin according to claim 1 wherein $R_3$ and $R_4$ form part of a further fused cycloaliphatic ring.

16. A curable resin according to claim 15 wherein the fused cycloaliphatic rings comprise five or six carbons.

17. A curable resin comprising a compound having the structure:

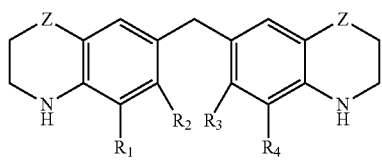

wherein Z is a carbon atom or a single bond and wherein $R_1$, $R_2$, $R_3$ and $R_4$ are H or a linear or branched $C_1$ to $C_5$ alkyl or wherein $R_1$ and $R_2$ form part of a further fused cycloaliphatic ring or wherein $R_3$ and $R_4$ form part of a further fused cycloaliphatic ring.

18. A curable resin according to claim 17 wherein $R_1$, $R_2$, $R_3$ and $R_4$ are H, said compound having the structure:

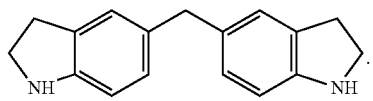 [SMILES: c1cc2c(cc1Cc1ccc3c(c1)CCN3)CCN2]

19. A curable resin according to claim 17 wherein $R_1$, $R_2$, $R_3$ and $R_4$ are H, said compound having the structure:

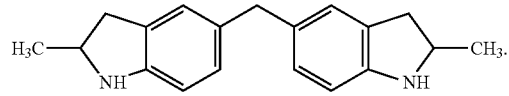 [SMILES: CC1Cc2cc(Cc3ccc4c(c3)CC(C)N4)ccc2N1]

* * * * *